(12) United States Patent
Alberico

(10) Patent No.: US 6,752,769 B2
(45) Date of Patent: Jun. 22, 2004

(54) CORE BITE BIOPSY NEEDLE

(75) Inventor: Ronald A. Alberico, East Amherst, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 10/162,250

(22) Filed: Jun. 4, 2002

(65) Prior Publication Data

US 2002/0198466 A1 Dec. 26, 2002

Related U.S. Application Data

(60) Provisional application No. 60/301,029, filed on Jun. 26, 2001.

(51) Int. Cl.[7] .................. A61B 10/00; A61B 17/34; A61M 5/32
(52) U.S. Cl. .............. 600/570; 600/564; 604/272; 606/185
(58) Field of Search .................. 604/272; 606/167, 606/180, 185; 600/562, 564, 566, 567, 570, 571

(56) References Cited

U.S. PATENT DOCUMENTS

| | | | |
|---|---|---|---|
| 4,600,014 A | 7/1986 | Beraha | 128/754 |
| 4,640,296 A | 2/1987 | Schnepp-Pesch et al. | 128/754 |
| 4,651,752 A | 3/1987 | Fuerst | 128/754 |
| 4,708,147 A | * 11/1987 | Haaga | 600/566 |
| 5,040,542 A | 8/1991 | Gray | 128/754 |
| 5,224,488 A | 7/1993 | Neuffer | 128/751 |
| 5,313,958 A | 5/1994 | Bauer | 128/754 |
| 5,492,130 A | 2/1996 | Chiou | 128/753 |
| 5,507,298 A | 4/1996 | Schramm et al. | 128/754 |
| 5,611,352 A | 3/1997 | Kobren et al. | 128/751 |
| 5,807,277 A | * 9/1998 | Swaim | 600/566 |
| 5,843,023 A | 12/1998 | Cecchi | 604/44 |
| 5,916,175 A | 6/1999 | Bauer | 600/567 |

FOREIGN PATENT DOCUMENTS

| | | | |
|---|---|---|---|
| EP | 0455626 A1 | * | 4/1991 |
| EP | 0 455 626 | | 11/1991 |
| GB | 2347862 | | 9/2000 |
| WO | 00/56220 | | 9/2000 |

* cited by examiner

*Primary Examiner*—Michael J. Hayes
*Assistant Examiner*—Catherine S. Williams
(74) *Attorney, Agent, or Firm*—Michael L. Dunn

(57) ABSTRACT

A biopsy needle that is based upon an opening at the tip of the needle, not the side, that permits the entire sample to be cut from the patient yet has smooth sides to reduce injury to the patient when the needle is inserted. The needle of the invention has a coaxial inner needle or tube that allows the opening at the tip to be completely closed and the sample or specimen to be cut off at its point of attachment after insertion of the needle. The needle of the invention samples tissue in front of the needle as it is pushed forward, rather than scraping tissue from the edges of the needle track. In accordance with the invention, the coaxial inner needle can be withdrawn and the sample obtained without moving the outer needle or tube. Several samples can thus be obtained with minimal need for repositioning the needle avoiding pain, tissue damage and risks associated with such repositioning.

2 Claims, 3 Drawing Sheets

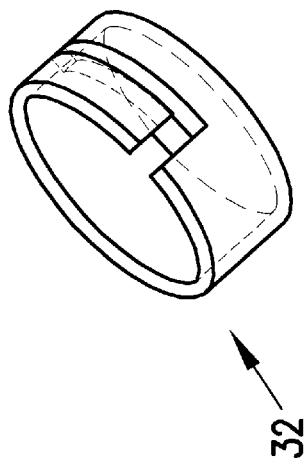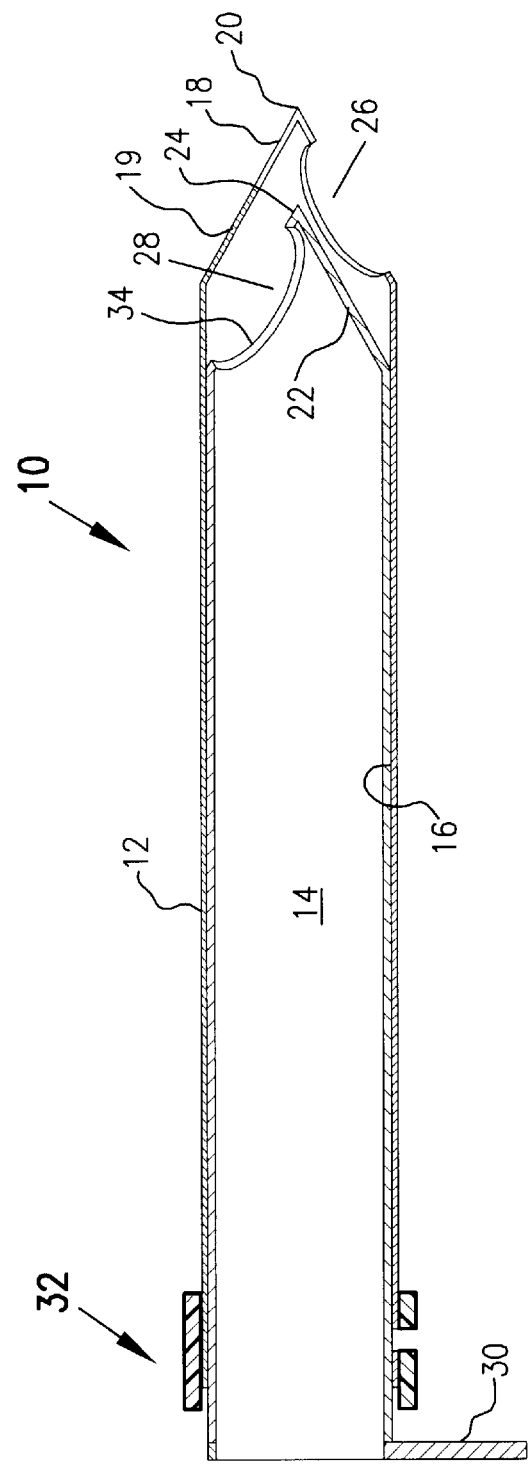

CORE BITE BIOPSY NEEDLE

This application claims priority from U.S. Provisional Patent Application No. 60/301,029 filed Jun. 26, 2001.

BACKGROUND OF THE INVENTION

This invention relates to biopsy needles and more particularly relates to needles that can cut a tissue sample internally within a patient and then withdraw the sample.

A number of biopsy needles for taking tissue samples are known but unfortunately such known needles have one or more serious disadvantages. Many of such needles, e.g. as described in U.S. Pat. Nos. 4,640,296; 5,040,542; 5,492,130; 5,843,023; 5,916,175; European Application 0 455 626; British Application 2 347 862 and International Application WO 00/56220 rely upon an open cutting edge of the needle which cuts around a sample and forces it into the needle. With such a configuration, the end of the sample is not severed but the operator must move the needle within the patient to finally tear the end of the sample from attached tissue. Such a procedure in a conscious patient can be extremely painful and traumatic and in any case can cause significant tissue damage to areas surrounding the removed sample. This unsatisfactory procedure is clearly illustrated in British patent application 2 347 862.

Another set of known biopsy needles does not cut at the tip of the needle but instead relies upon tissue overflowing into a side opening which is then cut off by a sliding sheath or other cutting means. Such needles are for example described in U.S. Pat. Nos. 4,600,014; 5,224,488; 5,313,958; 5,507,298; and 5,611,352. While such needles are an improvement in that the entire sample is cut rather than partially torn from a patient, there is another different problem associated with such needles. In particular, such needles rely upon tissue overflow into the side opening. The samples, if present at all, are thus irregular.

At least one attempt has been made to cut an entire sample while using an opening at the tip of the needle. Such an attempt is described in U.S. Patent No. 4,651,752. Unfortunately, the needle structure of U.S. Pat. No. 4,651,752 is complex with rough sides that can tear and bruise tissue and further would be very difficult to make in a small needle.

BRIEF DESCRIPTION OF THE DRAWINGS

FIG. 5 shows a perspective view of a hub detail of the needle of the invention.

FIG. 6 shows a cross sectional view of the needle with the inner needle partially withdrawn.

BRIEF DESCRIPTION OF THE INVENTION

Figure 1:
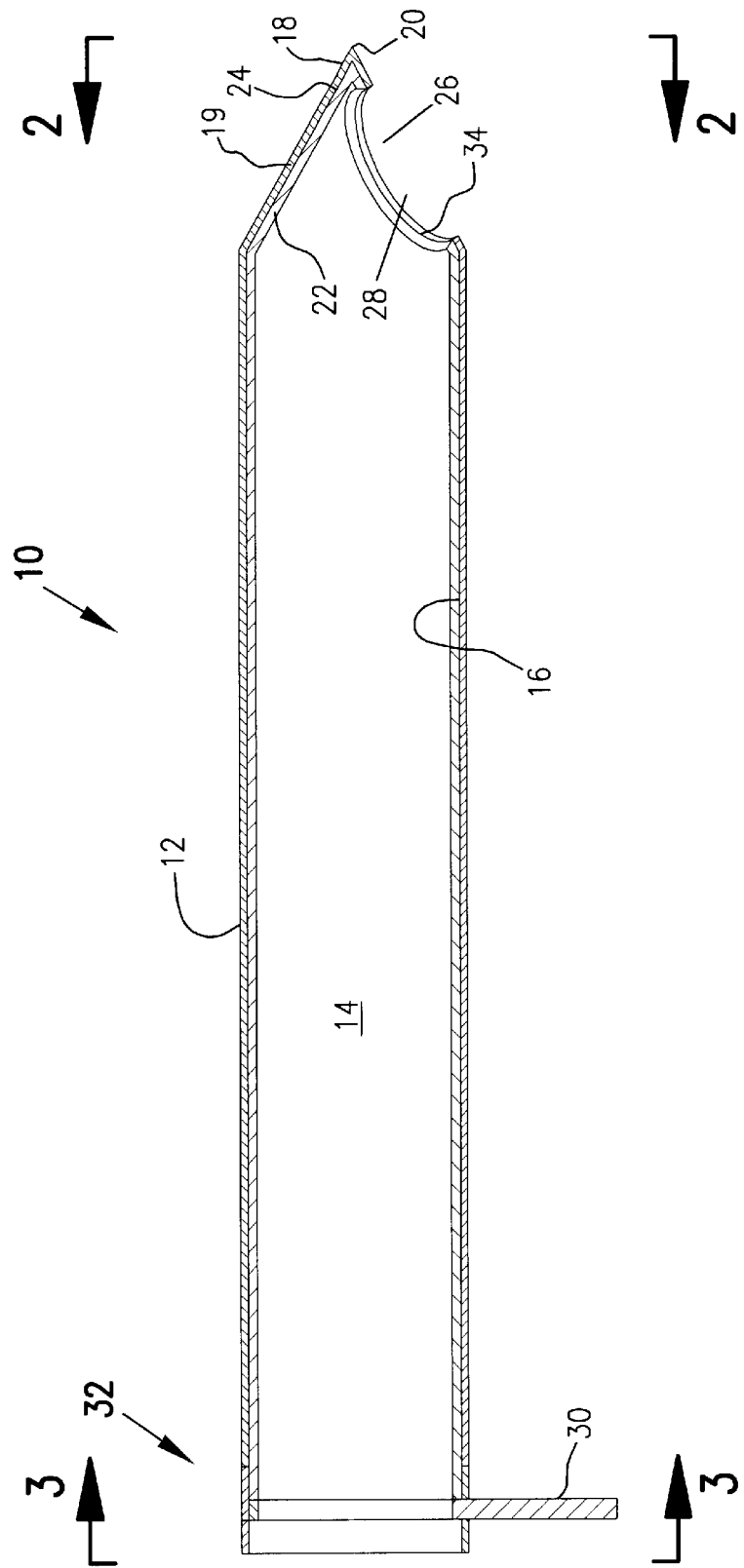
FIG. 1 shows a cross sectional view of a preferred embodiment of the biopsy needle of the invention.
Figure 4:
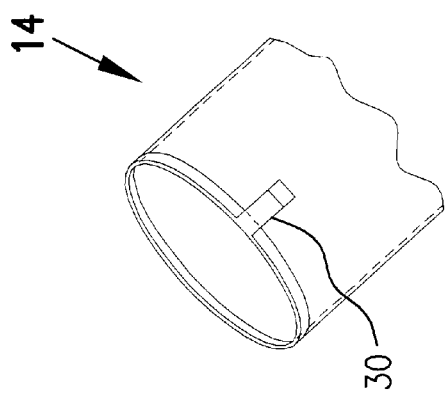
FIG. 4 shows a top side perspective view of the needle of FIG. 1.
Figure 3:
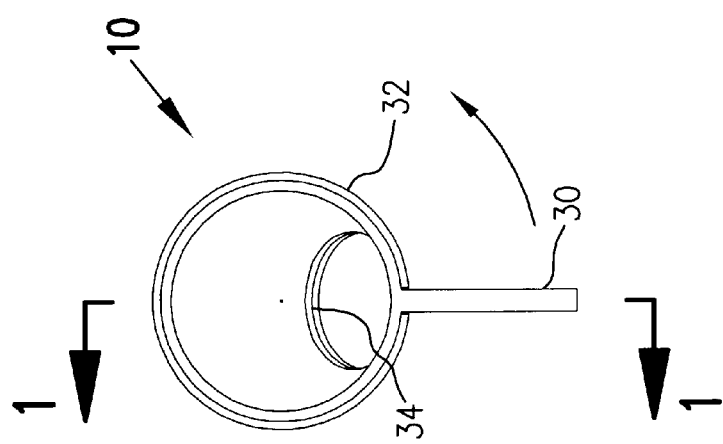
FIG. 3 shows a top end view of the needle of FIG. 1.
Figure 2:
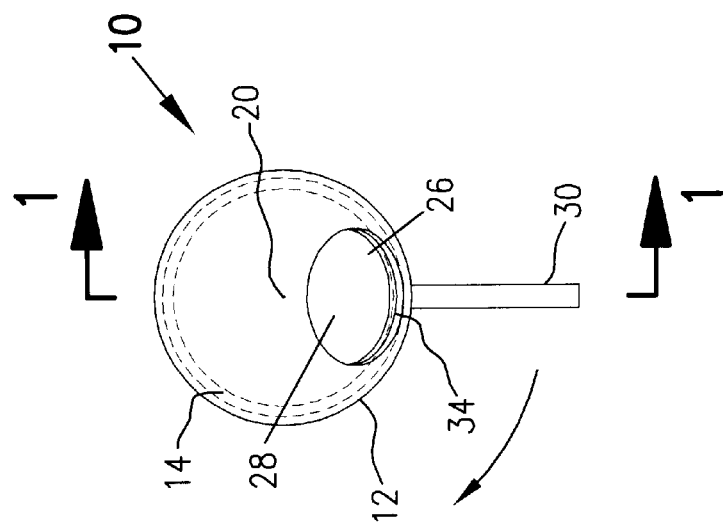
FIG. 2 shows a tip view of the needle of FIG. 1.

In accordance with the invention, there is therefore provided a biopsy needle that is based upon an opening at the tip of the needle, not the side, that permits the entire sample to be cut from the patient yet has smooth sides to reduce injury to the patient when the needle is inserted.

The needle of the invention has a coaxial inner needle or tube that allows the opening at the tip to be completely closed and the sample or specimen to be cut off at its point of attachment after insertion of the needle. The needle of the invention samples tissue in front of the needle as it is pushed forward, rather than scraping tissue from the edges of the needle track. In accordance with the invention, the coaxial inner needle can be withdrawn and the sample obtained without moving the outer needle or tube. Several samples can thus be obtained with minimal need for repositioning the needle avoiding pain, tissue damage and risks associated with such repositioning. Further, in closed position, the needle can be inserted through superficial tissue, pushing it to the side until a desired biopsy area is reached. The needle may then be opened near its point and further inserted to circumferentially cut a biopsy sample and the opening may then be closed to cut off the sample. Damage to superficial tissue and tissue in the area of the biopsy is thus minimized.

More particularly, the invention is a biopsy needle having an external hollow outer needle (tube) with a smooth side wall and an end with a point defined by at least one slanted end wall. The end wall is provided with an opening so that when the needle is inserted into biological tissue, tissue extends through the end opening in the external tube. An internal cutter, rotatable within the external hollow tube, is provided to cut a biological sample within said opening from its point of attachment and to close the opening upon making the cut.

In one embodiment, the internal cutter is an internal hollow tube fitting within the external hollow tube. The internal hollow tube has a shape corresponding with the shape of the external hollow tube, including an end opening corresponding with the end opening in the external hollow tube so that when the needle is inserted into biological tissue, tissue extends through the end openings in both the external tube and internal tube and rotation of the internal hollow tube cuts the tissue extending through the opening in the internal tube to obtain a cut sample and closes the opening in the external hollow tube to retain the cut sample.

The internal tube preferably slides within the external tube so that after a sample is cut, the internal tube can be withdrawn with the sample from the external tube without disturbing the position of the external tube.

DETAILED DESCRIPTION OF THE INVENTION

A preferred embodiment of the invention may be seen in the drawings. A biopsy needle 10 of the invention includes an outer needle or tube 12 and a coaxially rotatable corresponding inner needle or tube 14. The outer tube 12 is defined by a smooth sidewall 16 and an end 18 defined by a slanted end wall 19 with a point 20. The inner tube 14 has a corresponding end 22 with a point 24 sufficiently smaller in size to permit insertion within outer tube 12. Ends 18 and 22 are provided with openings 26 and 28 respectively. A handle 30 is provided that is attached to inner tube 14 to facilitate its rotation within a slot in a hub 32. The hub 32 attached to outer tube 12 holds and locks handle 30 in position to hold it longitudinally secure relative to outer tube 12 when inner tube 14 is rotated so that openings 26 and 28 are aligned. Hub 32 permits rotation of handle 30 and attached tube 14 so that an edge 34 of inner tube 14 can be moved to cut a sample and close openings 26 and 28 by relative opening offset. Handle 30 is however removable from hub 32 to permit withdrawal of handle 30 with attached inner tube 14 containing a sample, when opening 26 and 28 are offset. Such an offset position helps to retain the sample as inner tube 14 is removed.

It is to be understood that the invention also includes the method of taking a tissue sample using the biopsy needle of the invention.

What is claimed is:

1. A biopsy needle comprising an external hollow tube having a smooth side wall and an end with a point defined by at least one slanted end wall; wherein, said slanted end wall is provided with an opening so that when the needle is inserted into biological tissue, tissue extends through the opening in the external tube; and an internal cutter rotatable within the external hollow tube to cut a biological sample within said opening and to close said opening upon making said cut wherein the internal cutter is an internal hollow tube fitting within the external hollow tube, said internal hollow tube having a shape corresponding with the shape of the external hollow tube, including an end opening corresponding with the end opening in the external hollow tube so that when the needle is inserted into biological tissue, tissue extends through the end openings in both the external tube and internal tube and rotation of the internal hollow tube cuts the tissue extending through the opening in the internal tube to obtain a cut sample and closes the opening in the external hollow tube to retain the cut sample and wherein the internal tube slides within the external tube so that after a sample is cut, the internal tube can be withdrawn with the sample from the external tube.

2. The needle of claim 1 where the internal tube may be withdrawn with a cut sample without disturbing the position of the external tube.

* * * * *